(12) United States Patent
Chaouk et al.

(10) Patent No.: US 7,666,225 B2
(45) Date of Patent: Feb. 23, 2010

(54) SPINAL DISC NUCLEUS PULPOSUS IMPLANT

(76) Inventors: Hassan Chaouk, 10901 Burnt Mill Rd., Apt. # 1401, Jacksonville, FL (US) 32256; Bruktawit T. Asfaw, 3062 Wyntree Dr., Norcross, GA (US) 30071; Dennis W. Goupil, 3478 Dunlin Shore Ct., Norcross, GA (US) 30092

( * ) Notice: Subject to any disclaimer, the term of this patent is extended or adjusted under 35 U.S.C. 154(b) by 188 days.

(21) Appl. No.: 11/170,915

(22) Filed: Jun. 29, 2005

(65) Prior Publication Data

US 2005/0288789 A1 Dec. 29, 2005

Related U.S. Application Data

(60) Provisional application No. 60/583,852, filed on Jun. 29, 2004.

(51) Int. Cl.
*A61F 2/44* (2006.01)

(52) U.S. Cl. .................................................. 623/17.11

(58) Field of Classification Search ... 623/17.11–17.16; 424/486
See application file for complete search history.

(56) References Cited

U.S. PATENT DOCUMENTS

| | | | |
|---|---|---|---|
| 5,278,202 A | 1/1994 | Dunn et al. | |
| 5,410,016 A | 4/1995 | Hubbell et al. | |
| 5,490,984 A | 2/1996 | Freed | |
| 5,508,317 A | 4/1996 | Muller | |
| 5,514,379 A * | 5/1996 | Weissleder et al. | 424/426 |
| 5,529,914 A | 6/1996 | Hubbell et al. | |
| 5,844,016 A | 12/1998 | Sawhney et al. | |
| 5,902,599 A | 5/1999 | Anseth et al. | |
| 5,932,674 A * | 8/1999 | Muller | 526/266 |
| 5,981,826 A | 11/1999 | Ku et al. | |
| 6,028,164 A | 2/2000 | Loomis | |
| 6,060,534 A | 5/2000 | Ronan et al. | |
| 6,083,524 A | 7/2000 | Sawhney et al. | |
| 6,129,761 A | 10/2000 | Hubbell | |
| 6,153,211 A | 11/2000 | Hubbell et al. | |
| 6,156,345 A * | 12/2000 | Chudzik et al. | 424/484 |
| 6,162,844 A | 12/2000 | Lally et al. | |
| 6,166,130 A | 12/2000 | Rhee et al. | |
| 6,201,065 B1 | 3/2001 | Pathak et al. | |
| 6,265,509 B1 | 7/2001 | Muller | |
| 6,280,475 B1 * | 8/2001 | Bao et al. | 623/17.16 |
| 6,652,883 B2 | 11/2003 | Goupil et al. | |
| 6,676,971 B2 | 1/2004 | Goupil et al. | |
| 7,008,635 B1 * | 3/2006 | Coury et al. | 424/426 |

FOREIGN PATENT DOCUMENTS

| | | |
|---|---|---|
| EP | 730 847 | 9/1996 |
| WO | WO 97/22371 | 6/1997 |
| WO | WO 97/22372 | 6/1997 |
| WO | WO 99/12577 | 3/1999 |
| WO | WO 00/09087 | 2/2000 |
| WO | WO 00/23054 | 4/2000 |
| WO | WO 00/62827 | 10/2000 |
| WO | WO 00/64977 | 11/2000 |
| WO | WO 01/16210 | 3/2001 |
| WO | WO 01/17574 | 3/2001 |
| WO | WO 01/44307 | 6/2001 |
| WO | WO 02/16443 | 2/2002 |

OTHER PUBLICATIONS

Thanoo BC et al. J. Appl. Biomater. 2:67-72 (1991).
Thanoo BC et al., J. Pharm. Pharmacol. 45:16-20 (1993).

* cited by examiner

*Primary Examiner*—Thomas C Barrett
*Assistant Examiner*—Michael J Araj
(74) *Attorney, Agent, or Firm*—Collen A. Beard

(57) ABSTRACT

A prosthetic spinal disc nucleus pulposus formed from a hydrogel formed by crosslinking a macromer having a polymeric backbone comprising units with a 1,2-diol or 1,3-diol structure and at least two pendant chains bearing crosslinkable groups and an amphiphilic comonomer.

11 Claims, No Drawings

SPINAL DISC NUCLEUS PULPOSUS IMPLANT

RELATED APPLICATION

The present application is related to and claims priority to U.S. Provisional Application Ser. No. 60/583,852 filed Jun. 29, 2004, the entire contents of which are incorporated herein by reference.

BACKGROUND OF THE INVENTION

On occasion it becomes necessary to replace or augment a natural spinal disc nucleus pulposus with a prosthesis. For example, a spinal disc may become damaged due to trauma or disease resulting in a disc herniation. Such a prosthesis should preferably mimic the shape and function of the natural nucleus pulposus. Various types of prostheses have been designed, including hydrogels in the form of beads and solid implants. For example, U.S. Pat. No. 5,192,326 to Bao et al. discloses a prosthetic nucleus pulposus made of either a solid hydrogel core or a plurality of hydrogel beads surrounded by a membrane. The prosthesis is implanted in a dehydrated state and then hydrated to fill the intradiscal space.

Some prostheses include a constraining jacket to hold the prosthetic nucleus pulposus in place. However, such implants are large and require a large access point for insertion. To avoid this problem, implants have been proposed that rely on a composition that is inserted as a liquid and then hardens into a solid. U.S. Pat. No. 6,443,988 to Felt et al., for example, discloses an implant which includes a container that is inserted at the site of implantation and then filled with a material which is then cured in situ. The shape of this implant may be manipulated in situ and this implant may avoid problems of size and shape which would otherwise hinder implantation.

A similar prosthetic nucleus pulposus is disclosed in U.S. Pat. No. 6,187,048 to Milner et al. which discloses a spinal disc implant comprising a composition of acrylates which is injected into the intradiscal space and induced to at least partially polymerize through the addition of a cross-linking agent. This prosthesis, however, is similar in composition to joint implants, which eventually decompose and become mobile.

WO 01/68721 to BioCure, Inc. discloses a composition useful for tissue bulking that includes macromers having a backbone of a polymer having units with a 1,2-diol and/or 1,3-diol structure. Such polymers include poly(vinyl alcohol) (PVA) and hydrolyzed copolymers of vinyl acetate, for example, copolymers with vinyl chloride or N-vinylpyrrolidone. The backbone polymer contains pendant chains bearing crosslinkable groups and, optionally, other modifiers. The macromers form a hydrogel when crosslinked. This composition can be injected as a liquid and crosslinked into a solid hydrogel in situ.

The composition taught in WO 01/68721 results in a hydrogel that is suitable for many bio-applications. However, the hydrogel does not have the properties necessary for the particular and repeated stresses placed on a spinal disc nucleus pulposus.

SUMMARY OF THE INVENTION

The invention relates to a prosthetic spinal disc, more particularly to a prosthetic spinal disc nucleus pulposus. More specifically, the invention is a spinal disc nucleus pulposus implant formed from a composition including a crosslinkable macromonomer (also referred to herein as a macromer) and a comonomer that provides enhanced compressibility and integrity to the hydrogel.

DETAILED DESCRIPTION OF THE INVENTION

I. The Prosthetic Spinal Disc Nucleus Pulposus

In one aspect, the invention is a prosthetic spinal disc nucleus pulposus (referred to herein as an implant or prosthetic nucleus or prosthetic spinal disc nucleus) that is made from a crosslinkable macromer and an amphiphilic comonomer. The crosslinkable macromer and amphiphilic comonomer form a hydrogel that has properties that are ideal for use as a prosthetic spinal disc nucleus. The prosthesis can be used for either augmentation or replacement of the native nucleus. The prosthesis is preferably formed in situ.

The invention is also a method for making a prosthetic spinal disc nucleus from a crosslinkable macromer and an amphiphilic comonomer. In a preferred embodiment, the prosthetic nucleus is made in situ by injecting a liquid composition containing the crosslinkable macromer and amphiphilic comonomer into the spinal disc nucleus cavity and hardening the composition into a hydrogel. The method can involve either replacement or augmentation of the nucleus.

The prosthetic nucleus formed in situ conforms in shape to the nucleus space into which it is injected. The prosthetic nucleus has a compression modulus of approximately 3 mega pascals at 10-30% strain, a yield load of approximately 1000-6000 Newtons, a 60-70% strain at failure, and has the ability to withstand cyclic loading under physiologic conditions. Furthermore, it may be advantageous for the prosthetic nucleus to swell upon implantation to fill the nucleus space or to provide lift. Additional potential design features include adhesion to the native tissue and recoil after compression, for example 100% after approximately 30 minutes of relaxation.

The prosthetic nucleus is made using macromers similar to those described in WO 01/68721. It has been discovered, however, that the addition of certain comonomers gives the hydrogel unexpected properties making it more suitable for use as a prosthetic nucleus. The comonomers are described in detail below.

Macromers

The macromers have a backbone of a polymer comprising units with a 1,2-diol and/or 1,3-diol structure and at least two pendant chains including a crosslinkable group. The macromer backbone can optionally have other pendant chains containing modifiers.

Polyvinyl alcohols (PVAs) that can be used as the macromer backbone include commercially available PVAs, for example Vinol® 107 from Air Products (MW 22,000 to 31,000, 98 to 98.8% hydrolyzed), Polysciences 4397 (MW 25,000, 98.5% hydrolyzed), BF 14 from Chan Chun, Elvanol® 90-50 from DuPont and UF-120 from Unitika. Other producers are, for example, Nippon Gohsei (Gohsenol®), Monsanto (Gelvatol®), Wacker (Polyviol®), Kuraray, Deriki, and Shin-Etsu. In some cases it is advantageous to use Mowiol® products from Hoechst, in particular those of the 3-83, 4-88, 4-98, 6-88, 6-98, 8-88, 8-98, 10-98, 20-98, 26-88, and 40-88 types.

It is also possible to use copolymers of hydrolyzed or partially hydrolyzed vinyl acetate, which are obtainable, for example, as hydrolyzed ethylene-vinyl acetate (EVA), or vinyl chloride-vinyl acetate, N-vinylpyrrolidone-vinyl acetate, and maleic anhydride-vinyl acetate. If the macromer backbones are, for example, copolymers of vinyl acetate and vinylpyrrolidone, it is again possible to use commercially available copolymers, for example the commercial products available under the name Luviskol® from BASF. Particular examples are Luviskol VA 37 HM, Luviskol VA 37 E and Luviskol VA 28. If the macromer backbones are polyvinyl acetates, Mowilith 30 from Hoechst is particularly suitable.

The PVA preferably has a molecular weight of at least about 2,000. As an upper limit, the PVA may have a molecular weight of up to 300,000. Preferably, the PVA has a molecular weight of up to about 130,000, more preferably up to about 60,000, and especially preferably of about 14,000.

The PVA usually has a poly(2-hydroxy)ethylene structure. The PVA may also include hydroxy groups in the form of 1,2-glycols. The PVA can be a fully hydrolyzed PVA, with all repeating groups being —$CH_2$—CH(OH), or a partially hydrolyzed PVA with varying proportions (1% to 25%) of pendant ester groups. PVA with pendant ester groups have repeating groups of the structure $CH_2$—CH(OR) where R is $COCH_3$ group or longer alkyls, as long as the water solubility of the PVA is preserved. The ester groups can also be substituted by acetaldehyde or butyraldehyde acetals that impart a certain degree of hydrophobicity and strength to the PVA. For an application that requires an oxidatively stable PVA, the commercially available PVA can be broken down by $NaIO_4$—$KMnO_4$ oxidation to yield a small molecular weight (2000 to 4000) PVA.

The PVA is prepared by basic or acidic, partial or virtually complete, hydrolysis of polyvinyl acetate. In a preferred embodiment, the PVA comprises less than 50% acetate units, especially less than about 25% of acetate units. Preferred amounts of residual acetate units in the PVA, based on the sum of alcohol units and acetate units, are approximately from 3 to 25%.

The macromers have at least two pendant chains containing groups that can be crosslinked. Group is defined herein to include single polymerizable moieties, such as acrylates, as well as larger crosslinkable regions, such as oligomeric or polymeric regions. The crosslinkers are desirably present in an amount of from approximately 0.01 to 10 milliequivalents of crosslinker per gram of backbone (meq/g), more desirably about 0.05 to 1.5 milliequivalents per gram (meq/g). The macromers can contain more than one type of crosslinkable group.

The pendant chains are attached via the hydroxyl groups of the backbone. Desirably, the pendant chains having crosslinkable groups are attached via cyclic acetal linkages to the 1,2-diol or 1,3-diol hydroxyl groups. Desirable crosslinkable groups include (meth)acrylamide, (meth)acrylate, styryl, vinyl ester, vinyl ketone, vinyl ethers, etc. Particularly desirable are ethylenically unsaturated functional groups. A particularly desirable crosslinker is N-acryloyl-aminoacetaldehyde dimethylacetal (NAAADA) in an amount from about 6 to 21 crosslinkers per macromer.

Specific macromers that are suitable for use in the compositions are disclosed in U.S. Pat. Nos. 5,508,317, 5,665,840, 5,807,927, 5,849,841, 5,932,674, 5,939,489, and 6,011,077.

In one embodiment, units containing a crosslinkable group conform, in particular, to the formula I

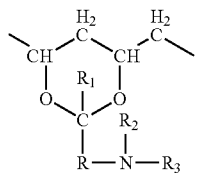

in which R is a linear or branched $C_1$-$C_8$ alkylene or a linear or branched $C_1$-$C_{12}$ alkane. Suitable alkylene examples include octylene, hexylene, pentylene, butylene, propylene, ethylene, methylene, 2-propylene, 2-butylene and 3-pentylene. Preferably lower alkylene R has up to 6 and especially preferably up to 4 carbon atoms. The groups ethylene and butylene are especially preferred. Alkanes include, in particular, methane, ethane, n- or isopropane, n-, sec- or tert-butane, n- or isopentane, hexane, heptane, or octane. Preferred groups contain one to four carbon atoms, in particular one carbon atom.

$R_1$ is hydrogen, a $C_1$-$C_6$ alkyl, or a cycloalkyl, for example, methyl, ethyl, propyl or butyl and $R_2$ is hydrogen or a $C_1$-$C_6$ alkyl, for example, methyl, ethyl, propyl or butyl. $R_1$ and $R_2$ are preferably each hydrogen.

$R_3$ is an olefinically unsaturated electron attracting copolymerizable radical having up to 25 carbon atoms. In one embodiment, $R_3$ has the structure

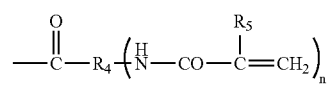

where $R_4$ is the

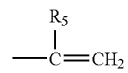

group if n=zero, or the

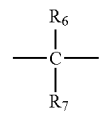

bridge if n=1;

$R_5$ is hydrogen or $C_1$-$C_4$ alkyl, for example, n-butyl, n- or isopropyl, ethyl, or methyl;

n is zero or 1, preferably zero; and $R_6$ and $R_7$, independently of one another, are hydrogen, a linear or branched $C_1$-$C_8$ alkyl, aryl or cyclohexyl, for example one of the following: octyl, hexyl, pentyl, butyl, propyl, ethyl, methyl, 2-propyl, 2-butyl or 3-pentyl. $R_6$ is preferably hydrogen or the $CH_3$ group, and $R_7$ is preferably a $C_1$-$C_4$ alkyl group. $R_6$ and $R_7$ as aryl are preferably phenyl.

In another embodiment, $R_3$ is an olefinically unsaturated acyl group of formula $R_8$—CO—, in which $R_8$ is an olefinically unsaturated copolymerizable group having from 2 to 24 carbon atoms, preferably from 2 to 8 carbon atoms, especially preferably from 2 to 4 carbon atoms. The olefinically unsaturated copolymerizable radical $R_8$ having from 2 to 24 carbon atoms is preferably alkenyl having from 2 to 24 carbon atoms, especially alkenyl having from 2 to 8 carbon atoms and especially preferably alkenyl having from 2 to 4 carbon atoms, for example ethenyl, 2-propenyl, 3-propenyl, 2-butenyl, hexenyl, octenyl or dodecenyl. The groups ethenyl and 2-propenyl are preferred, so that the group —CO—$R_8$ is the acyl radical of acrylic or methacrylic acid.

In another embodiment, the group $R_3$ is a radical of formula

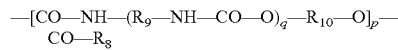

wherein p and q are zero or one and $R_9$ and $R_{10}$ are each independently lower alkylene having from 2 to 8 carbon atoms, arylene having from 6 to 12 carbon atoms, a saturated divalent cycloaliphatic group having from 6 to 10 carbon atoms, arylenealkylene or alkylenearylene having from 7 to 14 carbon atoms or arylenealkylenearylene having from 13 to 16 carbon atoms, and $R_8$ is as defined above.

Lower alkylene $R_9$ or $R_{10}$ preferably has from 2 to 6 carbon atoms and is especially straight-chained. Suitable examples include propylene, butylene, hexylene, dimethylethylene and, especially preferably, ethylene.

Arylene $R_9$ or $R_{10}$ is preferably phenylene that is unsubstituted or is substituted by lower alkyl or lower alkoxy, especially 1,3-phenylene or 1,4-phenylene or methyl-1,4-phenylene.

A saturated divalent cycloaliphatic group $R_9$ or $R_{10}$ is preferably cyclohexylene or cyclohexylene-lower alkylene, for example cyclohexylenemethylene, that is unsubstituted or is substituted by one or more methyl groups, such as, for example, trimethylcyclohexylenemethylene, for example the divalent isophorone radical.

The arylene unit of alkylenearylene or arylenealkylene $R_9$ or $R_{10}$ is preferably phenylene, unsubstituted or substituted by lower alkyl or lower alkoxy, and the alkylene unit thereof is preferably lower alkylene, such as methylene or ethylene, especially methylene. Such radicals $R_9$ or $R_{10}$ are therefore preferably phenylenemethylene or methylenephenylene.

Arylenealkylenearylene $R_9$ or $R_{10}$ is preferably phenylene-lower alkylene-phenylene having up to 4 carbon atoms in the alkylene unit, for example phenyleneethylenephenylene.

The groups $R_9$ and $R_{10}$ are each independently preferably lower alkylene having from 2 to 6 carbon atoms, phenylene, unsubstituted or substituted by lower alkyl, cyclohexylene or cyclohexylene-lower alkylene, unsubstituted or substituted by lower alkyl, phenylene-lower alkylene, lower alkylene-phenylene or phenylene-lower alkylene-phenylene.

The group —$R_9$—NH—CO—O— is present when q is one and absent when q is zero. Macromers in which q is zero are preferred.

The group —CO—NH—($R_9$—NH—CO—O)$_q$—$R_{10}$—O— is present when p is one and absent when p is zero. Macromers in which p is zero are preferred.

In macromers in which p is one, q is preferably zero. Macromers in which p is one, q is zero, and $R_{10}$ is lower alkylene are especially preferred.

All of the above groups can be monosubstituted or polysubstituted, examples of suitable substituents being the following: $C_1$-$C_4$ alkyl, such as methyl, ethyl or propyl, —COOH, —OH, —SH, $C_1$-$C_4$ alkoxy (such as methoxy, ethoxy, propoxy, butoxy, or isobutoxy), —NO$_2$, —NH$_2$, —NH($C_1$-$C_4$), —NH—CO—NH$_2$, —N($C_1$-$C_4$ alkyl)$_2$, phenyl (unsubstituted or substituted by, for example, —OH or halogen, such as Cl, Br or especially I), —S($C_1$-$C_4$ alkyl), a 5- or 6-membered heterocyclic ring, such as, in particular, indole or imidazole, —NH—C(NH)—NH$_2$, phenoxyphenyl (unsubstituted or substituted by, for example, —OH or halogen, such as Cl, Br or especially I), an olefinic group, such as ethylene or vinyl, and CO—NH—C(NH)—NH$_2$.

Preferred substituents are lower alkyl, which here, as elsewhere in this description, is preferably $C_1$-$C_4$ allyl, $C_1$-$C_4$ alkoxy, COOH, SH, —NH$_2$, —NH($C_1$-$C_4$ alkyl), —N($C_1$-$C_4$ alkyl)$_2$ or halogen. Particular preference is given to $C_1$-$C_4$ alkyl, $C_1$-$C_4$ alkoxy, COOH and SH.

For the purposes of this invention, cycloalkyl is, in particular, cycloalkyl, and aryl is, in particular, phenyl, unsubstituted or substituted as described above.

A particularly preferred macromer has a PVA backbone (14 kDa, 17% acetate incorporation) modified with 1.07 meq/g N-acrylamidoacetaldehyde dimethyl acetal (NAAADA) pendant polymerizable groups (about 15 crosslinks per chain). In some preferred embodiments the PVA backbone is also modified with a hydrophobic modifier acetaldehyde diethyl acetal (AADA) present in an amount from about 0 to 4 milliequivalents per gram (meq/g) of PVA (as discussed further below).

Comonomers

WO 01/68721 describes the addition of comonomers that are hydrophilic or hydrophobic to change the characteristics of the hydrogel. Surprisingly, it has been found that the inclusion of amphiphilic comonomers adds the qualities needed to make the hydrogel suitable for spinal disc nucleus replacement.

As used herein, the term amphiphilic means that one portion of the molecule is hydrophilic and one portion of the molecule is hydrophobic. In one embodiment, the hydrophilic portion is water soluble and the hydrophobic portion is not water soluble. The monomer as a whole is preferably wholly or partially water soluble. Examples of useful amphiphilic comonomers are diacetone acrylamide (DAA), N-vinyl caprolactam, N-(butoxymethyl)acrylamide, N-acroyl morpholine, crotonamide, N,N-dimethyl acrylamide, N-octadecylacrylamide, and acrylamide.

When the amphiphilic comonomers are copolymerized with the macromers described above, a hydrogel results that is more cohesive and has higher compressive strength than a hydrogel not containing the amphiphilic comonomer. Desirably, the comonomer is included in an amount ranging from about 5 to 95 weight percent, most preferably about 40-60 weight percent (where weight percent is the percent by weight of the total solution).

Crosslinking Initiators

The ethylenically unsaturated groups of the macromer and comonomer can be crosslinked via free radical initiated polymerization, including with initiation via photoinitiation, redox initiation, and thermal initiation. Systems employing these means of initiation are well known to those skilled in the art and may be used in the compositions taught herein. The desired amounts of the initiator components will be determined by concerns related to gelation speed, toxicity, extent of gelation desired, and stability.

In one embodiment, a two part redox system is employed. One part of the system contains a reducing agent. Examples of reducing agents are ferrous salts (such as ferrous gluconate dihydrate, ferrous lactate dihydrate, or ferrous acetate), cuprous salts, cerous salts, cobaltous salts, permanganate, manganous salts, and tertiary amines such as N,N,N,N-tetramethylethylene diamine (TMEDA). The other half of the solution contains an oxidizing agent such as hydrogen peroxide, t-butyl hydroperoxide, t-butyl peroxide, benzoyl peroxide, cumyl peroxide, potassium persulfate, or ammonium persulfate.

Either or both of the redox solutions can contain macromer, or it may be in a third solution. The solutions containing reductant and oxidant are combined to initiate the crosslinking. It may be desirable to use a coreductant such as ascorbate, for example, to recycle the reductant and reduce the amount needed. This can reduce the toxicity of a ferrous based system.

Thermal initiation can be accomplished using ammonium persulfate as the crosslinking initiator and optionally using N,N,N,N-tetramethylethylene diamine (TMEDA), which is an amine accelerator.

Modifier Groups

The macromers can include further modifier groups and crosslinkable groups. Some such groups are described in U.S. Pat. Nos. 5,508,317, 5,665,840, 5,807,927, 5,849,841, 5,932, 674, 5,939,489, and 6,011,077 and include hydrophobic modifiers such as acetaldehyde diethyl acetal (AADA), butyraldehyde, and acetaldehyde or hydrophilic modifiers such as N-(2,2-dimethoxy-ethyl) succinamic acid, amino acetaldehyde dimethyl acetal, and aminobutyraldehyde dimethyl acetal. These groups may be attached to the macromer backbone, or to other monomeric units included in the backbone. Crosslinkable groups and optional modifier groups can be bonded to the macromer backbone in various ways, for example through a certain percentage of the 1,3-diol units being modified to give a 1,3-dioxane, which contains a crosslinkable group, or a further modifier, in the 2-position. Modifiers include those to modify the hydrophobicity or hydrophilicity, active agents or groups to allow attachment of active agents, photoinitiators, modifiers to enhance or reduce adhesiveness, modifiers to impart thermoresponsiveness, modifiers to impart other types of responsiveness, and additional crosslinking groups.

Attaching a cellular adhesion promoter to the macromers can enhance cellular attachment or adhesiveness of the composition. These agents are well known to those skilled in the art and include carboxymethyl dextran, proteoglycans, collagen, gelatin, glucosaminoglycans, fibronectin, lectins, polycations, and natural or synthetic biological cell adhesion agents such as RGD peptides.

Having pendant ester groups that are substituted by acetaldehyde or butyraldehyde acetals, for example, can increase the hydrophobicity of the macromers and the formed hydrogel. One particularly useful hydrophobic modifying group is acetaldehyde diethyl acetal (AADA) present in an amount from about 0 to 4 milliequivalents per gram (meq/g) of PVA.

Hydrophilic modifiers such as —COOH in the form of N-(2,2-dimethoxy-ethyl) succinamic acid in an amount from about 0 to 2 meq/g PVA can be added to the composition to enhance performance of the composition, such as swelling.

It may also be desirable to include on the macromer a molecule that allows visualization of the formed hydrogel. Examples include dyes and molecules visualizable by magnetic resonance imaging.

Contrast Agents

The prosthetic nucleus can be made containing a contrast agent. A contrast agent is a biocompatible material capable of being monitored by, for example, radiography. The contrast agent can be water soluble or water insoluble. Examples of water soluble contrast agents include metrizamide, iopamidol, iothalamate sodium, iodomide sodium, and meglumine. Iodinated liquid contrast agents include Omnipaque®, Visipaque®, and Hypaque-76®. Examples of water insoluble contrast agents are tantalum, tantalum oxide, barium sulfate, gold, tungsten, and platinum. These are commonly available as particles preferably having a size of about 10 µm or less. Coated-fibers, such as tantalum-coated Dacron fibers can also be used.

The contrast agent is incorporated temporarily or permanently in the prosthetic implant. Both solid and liquid contrast agents can be simply mixed with a solution of the liquid composition prior to crosslinking of the macromers and comonomers. Liquid contrast agent can be mixed at a concentration of about 10 to 80 volume percent, more desirably about 20 to 50 volume percent. Solid contrast agents are desirably included in an amount of about 5 to 40 weight percent, more preferably about 5 to 20 weight percent.

Active Agents

The prosthetic nucleus can include an effective amount of one or more biologically or structurally active agents. It may be desirable to deliver the active agent from the formed hydrogel. Active agents that it may be desirable to deliver include prophylactic, therapeutic, diagnostic, and structural agents including organic and inorganic molecules and cells (collectively referred to herein as an "active agent" or "drug"). A wide variety of active agents can be incorporated into the hydrogel. Release of the incorporated additive from the hydrogel is achieved by diffusion of the agent from the hydrogel, degradation of the hydrogel, and/or degradation of a chemical link coupling the agent to the polymer. In this context, an "effective amount" refers to the amount of active agent required to obtain the desired effect.

Examples of active agents that can be incorporated include, but are not limited to, analgesics for the treatment of pain, for example ibuprofen, acetaminophen, and acetylsalicylic acid; antibiotics for the treatment of infection, for example tetracyclines and penicillin and derivatives; and additives for the treatment of infection, for example silver ions, silver (metallic), and copper (metallic).

Cells and tissue can be incorporated into the composition, including stem cells, autologous nucleus pulposus cells, transplanted autologous nucleus pulposus cells, autologous tissue, fibroblast cells, chondrocyte cells, notochordal cells, allograft tissue and cells, and xenograft tissue and cells.

It may be advantageous to incorporate material of biological origin or biological material derived from synthetic methods of manufacture such as proteins, polypeptides, polysaccharides, proteoglycans, and growth factors.

It may be desirable to include additives to improve the swelling and space-filling properties of the prosthetic disc, for example, dehydrated spheres, fibers, etc., hydrophilic polymers, such AMPS, etc., or hydrocolloids, such as agar, alginates, carboxymethylcellulose, gelatin, guar gum, gum arabic, pectin, starch, and xanthum gum.

Other additives that may prove advantageous are additives to improve the adhesive properties of the prosthetic disc, including positively charged polymers, such as Quat, etc., PVA modified with positive-charged moieties attached to the backbone, cyanoacrylates, PVA modified with cyanoacrylate moieties attached to the backbone, chitosan, and mussel-based adhesives.

Incorporation of additives to improve the toughness properties of the injectable disc materials may prove desirable such as low modulus spheres, fibers, etc that act as "crack arrestors" and high modulus spheres, fibers, etc that act as "reinforcing" agents.

Active agents can be incorporated into the composition simply by mixing the agent with the composition prior to administration. The active agent will then be entrapped in the hydrogel that is formed upon administration of the composition. Active agents can be incorporated into preformed articles through encapsulation and other methods known in the art and discussed further below. The active agent can be in compound form or can be in the form of degradable or non-degradable nano or microspheres. It some cases, it may be possible and desirable to attach the active agent to the macromer or to the preformed article. The active agent may also be coated onto the surface of the preformed article. The active agent may be released from the macromer or hydrogel over time or in response to an environmental condition.

Other Additives

It may be desirable to include a peroxide stabilizer in redox initiated systems. Examples of peroxide stabilizers are Dequest® products from Solutia Inc., such as for example Dequest® 2010 and Dequest® 2060S. These are phosphonates and chelants that offer stabilization of peroxide systems. Dequest® 2060S is diethylenetriamine penta(methylene phosphonic acid). These can be added in amounts as recommended by the manufacturer.

II. Methods of Making the Prosthetic Nucleus

To make the prosthetic nucleus, a liquid composition is prepared by mixing the amphiphilic comonomer, the macromer, and any other components such as a crosslinking initiator, in the desired concentrations for each and proportion to each other. The composition may be prepared as a two-part composition, which form the hydrogel when mixed together. In one embodiment, the macromer and comonomer are formed into a prosthesis prior to implantation. In another embodiment, the macromer and comonomer are crosslinked into the prosthetic nucleus in situ.

The spinal disc nucleus may have degenerated to the point where denucleation is not required. It may be desirable, however, to denucleate all or a portion of the disc nucleus prior to implantation of the prosthetic nucleus. This can be done by methods known in the field.

In the case of forming the prosthetic nucleus prior to administration, a mold may be used to shape the hydrogel, the hydrogel may be free-formed, or the hydrogel may be formed into articles, such as microspheres or rods, for example. The liquid composition is placed in a mold, if desired, and exposed to conditions to crosslink the macromer and comonomer. Microspheres can be made as described in WO 01/68721. The prosthetic nucleus is then implanted into the nucleus, which has been denucleated, if desired. Implantation of the pre-formed prosthesis can be by methods known in the art.

More desirably, the prosthetic nucleus is made by in situ crosslinking and hydrogel formation. After denucleation, if desired, an effective amount of the liquid composition is placed into the nucleus—preferably by a minimally invasive method. The term "effective amount", as used herein, means the quantity of composition needed to fill the disc nucleus cavity. The composition may be administered over a number of treatment sessions.

In the preferred method of making the prosthetic nucleus, the liquid composition is drawn up in a 10 ml Luer-lok syringe with care being taken to expel any air bubbles and then delivered using a needle of about 18 Gauge through the small annular access port into the denucleated disc space under fluoroscopic guidance until the disc space has been filled to the desired level. In the case of a two-part composition, the composition is mixed prior to injection in a syringe or using a dual syringe method-transferring the mixture back and forth between two 5 ml syringes using a three way stopcock with care being taken to avoid air bubbles. The composition will preferably crosslink into the formed hydrogel within 5 to 15 minutes post mixing.

The viscosity of the composition is, within wide limits, not critical, but the solution should preferably be a flowable solution that can be delivered through an appropriately sized catheter or syringe needle. For delivery through a microcatheter, a viscosity in the range of about 10 to 50 cp is desirable. The viscosity can be substantially higher for delivery through a syringe needle, such as, for example 20 to 300 cp without mechanical assistance or 100 to 500 cp with mechanical assistance. The viscosity will generally be controlled by the molecular weight of the macromers, the solids content of the solution, and the type and amount of contrast agent present (if any). The solids content of the solution will preferably range from about 2 percent by weight to about 30 percent by weight, desirably from about 6 to 12 percent by weight.

In the preferred embodiment, the composition should be injected before substantial crosslinking of the macromers has occurred. This prevents blockage of the syringe needle or catheter with gelled polymer. In addition, in situ crosslinking may allow anchoring of the hydrogel to host tissue by covalently bonding with collagen molecules present within the host tissue.

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric.

Example 1

Prior Art

PVA (mw=14,000) was modified with 0.45 mmol/g of N-acryloyl-aminoacetaldehyde dimethylacetal (NAAADA) as crosslinker (6.3 xl/chain). 10 g of a 20% (w/w) modified-PVA solution in water was mixed with 1 g of a 10% (w/w) solution of ammonium persulfate and then added to one barrel of a dual syringe applicator fitted with a 2 cm long mixing tip. Separately, 10 g of a 20% (w/w) aqueous modified-PVA solution was mixed with 50 µl of N,N,N,N-tetramethylethylene diamine (TMEDA) then placed in the second barrel of the dual syringe applicator. The mixture was injected into a disc mold wherein a polymer was quickly formed in about 20 seconds at room temperature. The disc was transparent, soft, and compressible but brittle.

Example 2

Use of Comonomer and Hydrophobic Modifier

PVA (mw=14,000) was modified with 1.07 mmol/g of N-acryloyl-aminoacetaldehyde dimethylacetal (NAAADA) as crosslinker (15 xl/chain), and 2.7 mmol/g of acetaldehyde diethyl acetal (AADA). 20 g of comonomer diacetone acrylamide (DAA) was slowly dissolved in 20 g of a 24% (w/w) PVA solution. 50 mg of ammonium persulfate was dissolved in 5 g of the resulting solution. 20 µl TMEDA was added and mixed for 20 seconds, then delivered into a disc mold. The resulting hydrogel was opaque-white and had a yield load of 4800 N.

Example 3

Use of Comonomer, Hydrophobic Modifier, and Hydrophilic Modifier

PVA (mw=14,000) was modified with 1.07 mmol/g of N-acryloyl-aminoacetaldehyde dimethylacetal (NAAADA) as crosslinker (15 xl/chain), 2.7 mmol/g of acetaldehyde diethyl acetal (AADA), and 0.5 mmol/g of aminoacetaldehydediethyl acetal. 20 g of comonomer DAA was slowly dissolved in 20 g of a 24% (w/w) PVA solution. 25 mg of ammonium persulfate was dissolved in 5 g of the resulting solution. 20 µl TMEDA was added and mixed for 20 seconds, then delivered into a disc mold. The resulting hydrogel was slightly opaque and had a yield load of 4600 N.

Example 4

Use of Comonomer, Hydrophobic Modifier, and Hydrophilic Modifier

PVA (mw=14,000) was modified with 1.07 mmol/g of N-acryloyl-aminoacetaldehyde dimethylacetal (NAAADA)

as crosslinker (15 xl/chain), 2.5 mmol/g of acetaldehyde diethyl acetal (AADA), and 1.0 mmol/g of N-(2,2-dimethoxy-ethyl)succinamic acid. 14 g of comonomer DAA was slowly dissolved in 20 g of a 24% (w/w) PVA solution. 25 mg of ammonium persulfate was dissolved in 5 g of the resulting solution. 20 μl TMEDA was added and mixed for 20 seconds, then delivered into a disc mold. The resulting hydrogel was translucent and has a yield load of 2700 N.

The following chart compares the results of examples 2-4:

| EX | hydrophobic modifier | hydrophilic modifier | yield load |
|----|----------------------|----------------------|------------|
| 2 | 2.7 mmol/g acetaldehyde diethyl acetal (AADA) | | 4800 N |
| 3 | 2.7 mmol/g acetaldehyde diethyl acetal (AADA) | 0.5 mmol/g aminoacetaldehydediethyl acetal | 4600 N |
| 4 | 2.5 mmol/g acetaldehyde diethyl acetal (AADA) | 1.0 mmol/g N-(2,2-dimethoxy-ethyl)succinamic acid. | 2700 N |

Example 5

Cadaver Testing

The same PVA macromer was used as in Example 2.5 g of the comonomer DAA was slowly dissolved in 5 g of a 24% (w/w) PVA macromer solution. 2.5 g of tantalum was added to the solution. 250 mg of ammonium persulfate was dissolved in the resulting solution. The solution was mixed for 4 minutes. 25 μl TMEDA was added and mixed for 2 minutes. The solution was then pulled into a 10 ml syringe and about 5 ml was delivered into a fresh cadaver lumbar segment through an 18 G needle.

The cadaver segment had previously been tested for range of motion in the intact condition and again after denucleation. Prior to each test, the cadaver segment was pre-conditioned at 300±50 N at 1 Hz for 1000 cycles. Compression testing was conducted at 0 to 600 N. Flexion, extension and bending were tested at 0 to 600 N at 3 cm off center. Rotation was tested at 6 Nm at a rate of 2 Nm/sec.

The results of the testing indicate that the prosthetic nucleus pulposus restored the cadaver segment to near intact condition as shown in the following table.

| Test | Units | Intact (as received) | After Denucleation | After Polymer Injection |
|------|-------|----------------------|--------------------|-----|
| Compression | mm/1000 N | 1.29 | 1.39 | 1.41 |
| Extension | mm/1000 N | 2.55 | 3.00 | 2.16 |
| Flexion | mm/1000 N | 4.88 | 2.93 | 4.37 |
| L Lateral Bend | mm/1000 N | 4.53 | 3.01 | 4.22 |
| R Lateral Bend | mm/1000 N | 3.25 | 2.32 | 4.09 |
| L Rotation | deg × 10/N–m | 2.78 | 3.96 | 2.93 |
| R Rotation | deg × 10/N–m | 3.62 | 4.14 | 3.73 |

Example 6

Comparison of Comonomer Concentration

The following chart compares the effect of comonomer concentration on yield load. The comonomer was diacetone acrylamide (DAA).

| PVA:DAA | yield load |
|---------|------------|
| 1:1 | 4289 |
| 1:0.7 | 2385 |
| 1:0.6 | 1294 |
| 1:0.5 | 1015 |

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A spinal disc nucleus pulposus prosthesis comprising a hydrogel formed from a macromer and an amphiphilic comonomer, wherein the macromer has a poly(vinyl alcohol) (PVA) backbone having a molecular weight of about 100,000 to about 150,000, and pendant chains bearing crosslinkable groups in an amount of about 0.05 to 1.5 milliequivalents crosslinker per gram of backbone, wherein the comonomer is present at a concentration between about 40-60% by weight, and wherein the PVA backbone is modified with a hydrophobic modifier comprising acetaldehyde diethyl acetal (AADA) present in an amount of about 2.5 to 4.0 milliequivalents per gram (meq/g) of PVA.

2. The prosthesis of claim 1, wherein the hydrogel has the shape of the spinal disc nucleus cavity.

3. The prosthesis of claim 1, wherein the comonomer is selected from the group consisting of diacetone acrylamide (DAA), N-vinyl caprolactam, N-(butoxymethyl)acrylamide, N-acroyl morpholine, crotonamide, N,N-dimethyl acrylamide, N-octadecylacrylamide, and acrylamide.

4. The prosthesis of claim 1, wherein the comonomer is DAA.

5. The prosthesis of claim 4, wherein the PVA backbone has a molecular weight of about 130,000 and the pendant chains bearing crosslinkable groups are N-acrylamidoacetaldehyde dimethyl acetal (NAAADA) in an amount of about 0.34 milliequivalents crosslinker per gram of PVA.

6. The prosthesis of claim 1, wherein the PVA backbone further is modified with a second hydrophobic modifier or a hydrophilic modifier.

7. A method for replacing or augmenting a spinal disc nucleus pulposus in a spinal disc nuclear cavity with a prosthesis comprising implanting into the spinal disc nuclear cavity a hydrogel formed from a macromer and an amphiphilic comonomer; wherein the macromer has a PVA backbone with a molecular weight of about 100,000 to about 150,000, and pendant chains bearing crosslinkable groups in an amount of about 0.05 to 1.5 milliequivalents crosslinker per gram of backbone, wherein the comonomer is present at a concentration between about 40-66% by weight and wherein the prosthesis is formed in situ.

8. The method of claim 7, wherein the native spinal disc nucleus pulposus is partially or completely removed prior to implanting the prosthesis.

9. The method of claim 7, wherein the spinal disc has a nuclear cavity surrounded by an annulus and wherein the macromer and comonomer are combined in solution along with a free radical crosslinking initiator and injected into the spinal disc nuclear cavity as a solution.

10. The method of claim 9, wherein the step of implanting comprises injecting the solution through the annulus using a needle of about 18 Gauge.

11. A spinal disc nucleus pulposus prosthesis comprising a hydrogel formed from a macromer and an amphiphilic comonomer;
- wherein the macromer has a poly(vinyl alcohol) (PVA) backbone having a molecular weight of about 130,000 and pendant chains bearing crosslinkable groups in an amount of about 0.34 milliequivalents crosslinker per gram of PVA;
- wherein the amphiphilic comonomer is diacetone acrylamide (DAA) at a concentration between about 40-60% by weight;
- wherein the crosslinkable groups are N-acrylamidoacetaldehyde dimethyl acetal (NAAADA); and
- wherein the PVA backbone further is modified with a hydrophobic modifier comprising acetaldehyde diethyl acetal (AADA) present in an amount of about 2.5 to 4.0 milliequivalents per gram (meq/g) of PVA.

* * * * *